(12) United States Patent
Rowlen et al.

(10) Patent No.: US 10,031,061 B2
(45) Date of Patent: Jul. 24, 2018

(54) FLOW MEASUREMENT AND CONTROL FOR IMPROVED QUANTIFICATION OF PARTICLES IN FLOW CYTOMETRY

(75) Inventors: Kathy L. Rowlen, Longmont, CO (US); Matthew Ferris, Louisville, CO (US)

(73) Assignee: IntelliCyt Corporation, Albuquerque, NM (US)

( * ) Notice: Subject to any disclaimer, the term of this patent is extended or adjusted under 35 U.S.C. 154(b) by 0 days.

(21) Appl. No.: 13/319,662

(22) PCT Filed: May 13, 2009

(86) PCT No.: PCT/US2009/043811
§ 371 (c)(1),
(2), (4) Date: Nov. 23, 2011

(87) PCT Pub. No.: WO2010/132053
PCT Pub. Date: Nov. 18, 2010

(65) Prior Publication Data
US 2012/0070818 A1    Mar. 22, 2012

(51) Int. Cl.
*G01N 15/10*    (2006.01)
*G01N 15/14*    (2006.01)

(52) U.S. Cl.
CPC ......... *G01N 15/14* (2013.01); *G01N 15/1404* (2013.01)

(58) Field of Classification Search
None
See application file for complete search history.

(56) References Cited

U.S. PATENT DOCUMENTS

| | | | |
|---|---|---|---|
| 5,040,890 A * | 8/1991 | North, Jr. | 356/72 |
| 5,245,318 A * | 9/1993 | Tohge et al. | 340/611 |
| 5,306,467 A * | 4/1994 | Douglas-Hamilton et al. | 422/551 |
| 5,351,118 A | 9/1994 | Spinell | |
| 5,374,398 A | 12/1994 | Isami et al. | |
| 5,395,588 A | 3/1995 | North, Jr. et al. | |
| 5,483,469 A | 1/1996 | Van Den Engh et al. | |
| 5,602,039 A | 2/1997 | Van Den Engh | |
| 5,690,895 A | 11/1997 | Matsumoto et al. | |
| 5,895,764 A | 4/1999 | Sklar et al. | |

(Continued)

FOREIGN PATENT DOCUMENTS

JP    2008534947 A    8/2008

OTHER PUBLICATIONS

Hercher et al., Detection and Discrimination of Individual Viruses by Flow Cytometry, 1979, The Journal of Histochemistry and Cytochemistry, vol. 27, No. 1., pp. 350-352.*

(Continued)

*Primary Examiner* — P. Kathryn Wright
(74) *Attorney, Agent, or Firm* — Marsh Fischmann & Breyfogle LLP (57) ABSTRACT

The present invention relates to methods that enable improved accuracy for quantitative particle counting in a flowing liquid stream. The methods of the present invention utilize the real-time measurement of flow rates and flow rate control through feedback mechanisms to improve quantification, and this improved quantification translates to more accurate particle counting. In certain embodiments, particles being counted are biological particles in a liquid sample, such as viruses.

1 Claim, 8 Drawing Sheets

(56) References Cited

U.S. PATENT DOCUMENTS

| | | |
|---|---|---|
| 6,183,697 B1 | 2/2001 | Tanaka et al. |
| 6,248,590 B1 | 6/2001 | Malachowski |
| 6,256,096 B1 | 7/2001 | Johnson |
| 6,432,630 B1 | 8/2002 | Blankenstein |
| 6,550,324 B1 | 4/2003 | Mayer et al. |
| 6,589,792 B1 | 7/2003 | Malachowski |
| 6,592,822 B1 | 7/2003 | Chandler |
| 6,597,438 B1 | 7/2003 | Cabuz et al. |
| 6,813,944 B2 | 11/2004 | Mayer et al. |
| 6,878,556 B2 | 4/2005 | Sklar et al. |
| 6,880,414 B2 | 4/2005 | Norton |
| 6,890,487 B1 | 5/2005 | Sklar et al. |
| 7,016,022 B2 | 3/2006 | Fritz et al. |
| 7,061,595 B2 | 6/2006 | Cabuz et al. |
| 7,277,166 B2 | 10/2007 | Padmanabhan et al. |
| 7,307,721 B2 | 12/2007 | King |
| 7,318,336 B2 | 1/2008 | Roth et al. |
| 7,355,696 B2 | 4/2008 | Mueth et al. |
| 7,368,084 B2 | 5/2008 | Sklar et al. |
| 7,420,659 B1 | 9/2008 | Cabuz et al. |
| 7,452,725 B2 | 11/2008 | Leary et al. |
| 7,471,394 B2 | 12/2008 | Padmanabhan et al. |
| 7,485,153 B2 | 2/2009 | Padmanabhan et al. |
| 7,553,453 B2 | 6/2009 | Gu et al. |
| 7,671,987 B2 | 3/2010 | Padmanabhan et al. |
| 7,688,427 B2 | 3/2010 | Cox et al. |
| 7,691,636 B2 | 4/2010 | Frazier et al. |
| 7,758,811 B2 | 7/2010 | Durack et al. |
| 7,776,268 B2 | 8/2010 | Rich |
| 7,780,916 B2 | 8/2010 | Bair et al. |
| 7,817,276 B2 | 10/2010 | Kiesel et al. |
| 7,978,329 B2 | 7/2011 | Padmanabhan et al. |
| 7,981,661 B2 | 7/2011 | Rich |
| 8,017,402 B2 | 9/2011 | Rich |
| 8,071,051 B2 | 12/2011 | Padmanabhan et al. |
| 8,134,705 B2 | 3/2012 | Kaduchak et al. |
| 8,182,767 B2 | 5/2012 | Padmanabhan et al. |
| 8,187,888 B2 | 5/2012 | Rich |
| 8,202,733 B1 * | 6/2012 | Javadi .................. 436/180 |
| 8,262,990 B2 | 9/2012 | Bair et al. |
| 8,263,955 B2 | 9/2012 | Kiesel et al. |
| 8,273,294 B2 | 9/2012 | Padmanabhan et al. |
| 8,283,177 B2 | 10/2012 | Ball et al. |
| 2005/0105077 A1* | 5/2005 | Padmanabhan et al. ....... 356/39 |
| 2005/0255001 A1* | 11/2005 | Padmanabhan et al. ....... 422/73 |
| 2006/0163119 A1 | 7/2006 | Hirano et al. |
| 2008/0152542 A1 | 6/2008 | Ball et al. |
| 2008/0195020 A1 | 8/2008 | Cabuz et al. |
| 2008/0252884 A1 | 10/2008 | Carr |
| 2009/0029870 A1 | 1/2009 | Ward et al. |
| 2009/0104075 A1 | 4/2009 | Rich |
| 2009/0105963 A1 | 4/2009 | Laursen et al. |
| 2009/0107057 A1 | 4/2009 | Hansort |
| 2010/0319469 A1 | 12/2010 | Rich |
| 2012/0077260 A1 | 3/2012 | Sharon et al. |
| 2012/0140205 A1 | 6/2012 | Kaduchak et al. |

OTHER PUBLICATIONS

Honeywell Introduces High-Performance, Liquid Nano-Flow Sensor, Jul. 30, 2004, (www.automation.com/automation-news/industry/honeywell-introduces-high-performance-liquid-nano-flow-sensor#).*

Virus quantification from Wikipedia,http://en.wikipedia.org/wiki/Virus_quantification, citing Stoffel, C.L.; Finch, R.; Christensen, K.; Edwards, D.; Rowlen, K.L. (2005). "Rapid Determination of Baculovirus Titer by a Dual Channel Virus Counter". American Biotechnology Laboratory 37 (22): 24-25.*

Stoffel, C.L.; Finch, R.; Christensen, K.; Edwards, D.; Rowlen, K.L. (2005). "Rapid Determination of Baculovirus Titer by a Dual Channel Virus Counter". American Biotechnology Laboratory 37 (22): 24-25.*

Notification of Transmittal of the International Search Report and the Written Opinion of the International Searching Authority, or the Declaration re International Application No. PCT/US2009/043811, dated Feb. 19, 2010, 14 pps.

Notification of Transmittal of International Preliminary Report on Patentability re International Application No. PCT/US09/43811, dated Oct. 20, 2011, 19 pps.

U.S. Appl. No. 61/110,427, filed Aug. 29, 2000, Uffenheimer.

* cited by examiner

FLOW MEASUREMENT AND CONTROL FOR IMPROVED QUANTIFICATION OF PARTICLES IN FLOW CYTOMETRY

STATEMENT REGARDING FEDERALLY SPONSORED RESEARCH OR DEVELOPMENT

This invention was made with Government support under Grant No. R43 AI-068270 awarded by NIH/NIAID. The Government has certain rights in the invention.

BACKGROUND

Flow cytometry is an established commercial technique with many applications including common use in hematology and immunology. As the name itself implies, flow cytometry involves the analysis (i.e. measurement of physical and/or chemical properties) of single biological or non-biological particles as they pass (i.e. flow) through a probe region within a flow cell. A variety of methods including electrical, acoustic, and optical methods are used to detect and characterize particles as they flow through the probe region. The information gathered can be used to determine if a certain type of particle is present, how many particles are present, characteristics of the particles, or relative distributions of particles within a mixed population. Furthermore, many flow cytometers (called cell sorters) have the ability to segregate particles as they are examined based on the real-time analysis of their properties.

A person of ordinary skill in the art will be familiar with the typical operation of a flow cytometer in which the sample is first pumped via mechanical pump or gas pressure into a flow cell. Within the flow cell, the sample is commonly shaped into a narrow stream or stream of droplets by a sheath medium (either liquid or gas). By shaping the sample stream, individual particles in the sample are allowed to pass, one at a time, through a probe region where they are interrogated. One common method is optical interrogation, in which the particles intersect a focused laser beam or multiple collinear laser beams. Particle interactions with the laser(s) are monitored by one or more detectors that are used to quantify detectable properties such as forward or side light scattering or fluorescence at any number of specific wavelengths. Signal amplitudes from the detector(s) are quantified for each particle and characteristic signals are used to identify or categorize particles. Simple commercial instruments may have a single laser and monitor forward and side scattering along with one fluorescence wavelength, whereas research level flow cytometers may have four or more lasers for excitation and 10 or more detection channels capable of measuring forward scattering, side scattering, and several fluorescence wavelengths. The data generated from each detection channel can be analyzed alone or in combination with data from a number of other channels. In a well-designed experiment, this multi-parametric analysis can reveal a large amount of information, but can also entail a significant amount of complicated data processing and interpretation.

Typical commercially-available flow cytometers are advantageous for certain applications in terms of the high information content gained, but are generally limited to analyzing particles that are relatively large, that is, on the order of the size of a bacterium or cell. Although analysis of other size ranges with traditional flow cytometers is possible through special experimental optimization, analysis of size ranges between 1-15 microns is typical. In addition, typical flow cytometers are not routinely used for the accurate quantification of biological particles, as they are generally utilized to obtain more specific information as outlined below. Examples of more typical analyses familiar to one skilled in the art would be the identification of several different populations of cells within a blood specimen (for example, determining populations of lymphocytes, monocytes, and neutrophils by correlating forward and side scattering data), and the evaluation of cell-surface markers by immunologists through the use of fluorescently-labeled antibodies.

Viruses are a type of biological particle that require accurate enumeration, but their small particle size of between ten and several hundred nanometers excludes them from analysis using typical flow cytometry. Some of the traditional methods used to count virus particles include plaque assay, epifluorescence microscopy (EFM), and transmission electron microscopy (TEM). The plaque assay is a quantitative tissue culture method developed in 1952. While plaque assays remain the gold standard for virus quantification, the technique is relatively inaccurate and imprecise, giving rise to ~25% relative error even when conducted by highly trained individuals. In addition, plaque assays are limited to viruses that are lysogenic, and they require skill, are labor intensive, and the time to result is from 12 hrs to 2 weeks. EFM is a technique in which virus particles are concentrated, stained with a highly fluorescent dye, and imaged optically. Drawbacks to EFM include the low resolution of the resulting optical image and the incapability of discriminating between infectious and non-infectious viral particles. TEM can provide high spatial resolution and morphological information, but samples must be interrogated under high vacuum conditions that are irrelevant for biological samples. In addition, TEM is expensive, and not widely available.

There are limited examples of the use of typical commercially-available flow cytometers to enumerate free viruses in solution. Brussaard notes previous studies detailing the use of commercially-available flow cytometers to enumerate marine viruses (Brussaard, C. P. D. Appl. Envir. Microbiol., 2004, 70(3), 1506-1513 and references cited therein). These studies have generally used expensive commercially-available flow cytometers, and have analyzed particle sizes much larger than a typical virus. None of these studies utilized the measurement or measurement and control of flow rates to improve accuracy of particle enumeration. An alternative flow cytometric approach to the enumeration of nanometer-sized particles including viruses has been described by Ferris et al. (Ferris, M. M., Rowlen, K. L. Rev. Sci. Instrum. 2002, 73(6), 2404-2410 and Ferris et al. Anal Chem, 2002, 74, 1849-1856). A simple, rapid, and inexpensive single channel flow cytometer was developed and specifically optimized for virus enumeration. This example did not utilize a sheath fluid to achieve hydrodynamic focusing of the sample fluid as is common in traditional flow cytometry. Instead, a confocal detection geometry similar to that used in single molecule detection studies was utilized. A simple glass capillary was used as the flow cell, and a syringe pump supplied the sample pressure. The instrument and method were validated first by enumerating well-characterized fluorescent spheres with diameters from 26 to 2600 nm, encompassing the size range of most typical viruses. This experimental configuration was then used to enumerate three distinct respiratory viruses: adenovirus, respiratory syncytial virus, and influenza A virus. Signal amplitude was found to scale with nucleic acid content, and the values correlated with values obtained from other standard detection methods. One shortcoming of this single color detection scheme is that this configuration does not allow the differentiation between whole virus particles and broken or partial particles. This single channel detection approach tends to overestimate the intact particle count in a sample due to this lack of discrimination, and this was confirmed by comparison to tissue culture (which only measures infectious viral particles). Other drawbacks to this method include the need for post-acquisition data analysis (results were not generated in real-time) and that the instrumental configuration was not amenable to routine manufacturing for commercialization. In addition, the glass capillary flow cell was susceptible to clogging.

A dual channel flow cytometer optimized specifically for counting intact (whole) virus particles has been described (Stoffel, Finch, and Rowlen, Cytometry Part A, 2005, 65A: 140-147; Stoffel et al., Am. Biotech. Lab., 2005, 23(12), 24-25). An extension of the design of Ferris et al. described above, this instrument utilized a two-color detection method by adding a second detection channel. The genomic material (DNA/RNA) and protein of baculovirus were differentially stained. The two fluorescent dyes were excited with a single wavelength, and the fluorescence emission from each stain was then collected on separate channels. Simultaneous events occurring on both channels were used to indicate intact virus particles, and this enumeration technique showed a direct correlation to traditional plaque titer methods. Although this method of enumeration allowed better discrimination of whole virus particles, the instrument was a research instrument and was not amenable to routine manufacturing for commercialization and suffered from the same periodic clogging of the capillary flow cell as described in the single channel instrument above. In addition, all of the data processing and analysis for this system was conducted after the sample had been processed (Stoffel and Rowlen *Anal. Chem.* 2005, 77(7), 2243-224), and required user input to multiple software packages. This post-acquisition data analysis is the typical method used in traditional flow cytometric applications. Fast analog-to-digital converters and digitizing systems are used to acquire and store data for further analysis after the sample run is complete. The user sets limits and ranges for every channel of information and can process the data in a variety of ways using sophisticated software packages, relying on user expertise to apply appropriate settings. In most cases, the user must wait until the run is complete, process the data, and only then determine that the settings were or were not appropriate for the sample. The primary disadvantages to these sophisticated flow cytometer research tools include the need for user expertise, analysis time, and cost.

As mentioned previously, traditional flow cytometers are generally not used for accurate particle quantification. Flow control is typically achieved through the use of one of several types of pumps that are configured to supply a constant pressure. Although a constant pressure is being delivered, a number of variables may ultimately affect the flow rates, and in turn negatively affect particle quantification.

The recent commercial availability of small mass flow sensors capable of accurately measuring low liquid flow rates in the nL/min to µL/min range enable new possibilities in terms of inexpensive liquid flow handling. U.S. Pat. Nos. 6,550,324 and 6,813,944 describe small CMOS-based mass flow devices comprised of calorimetric microsensors placed along a tube containing flowing liquid. A heating element on the CMOS sensor applies a small amount of heat to the flowing liquid, and two temperature sensors positioned above and below the heat source measure temperature, and the temperature differences are then related to the flow rate of the liquid. U.S. Pat. No. 6,597,438 describes a portable flow cytometer into which this type of thermal anemometric flow sensor has been incorporated, but particle quantification was not demonstrated, as the mass flow sensor was incorporated for the purposes of reducing overall size, complexity, and power consumption of the handheld device.

In spite of the improvements made in the area of enumeration of virus particles by incorporating aspects of traditional flow cytometry with different experimental configurations that allow better discrimination and improved quantification, there is a need in the art to further improve viral quantification methods. Specifically, new devices and methods capable of replacing the long-used but labor and time intensive gold standard methods require high counting accuracy, rapid time to result, and ease of use in a typical laboratory setting.

SUMMARY OF THE INVENTION

The present invention provides a method to enable accurate, rapid enumeration of particles in a flowing steam in a routine laboratory setting. In some embodiments, the method of the present invention incorporates flow rate measurement in real time for the purpose of improving accuracy of particle quantification. In some embodiments, the method incorporates flow rate measurement in real time and feedback controlled flow rate adjustment for the purpose of improving accuracy of particle quantification. In some embodiments, the method of the present invention incorporates real-time data analysis that enables quantitative evaluation of the number of events on each detection channel independently as well as the number of events observed simultaneously on both channels, providing an instantaneous result to the user that specifies the number of particles per unit volume. In an embodiment, the particles in a flowing steam are biological particles such as viruses.

BRIEF DESCRIPTION OF THE DRAWINGS

A better understanding of the present invention will be had upon reference to the following detailed description read in conjunction with the accompanying drawings. In the accompanying drawings, like reference characters refer to like parts throughout, and wherein.

DETAILED DESCRIPTION OF THE INVENTION

These and other features and advantages of the described invention reside in the construction of parts and the combination thereof, and the mode of operation and use, as will become apparent from the following description and examples, reference being made to the accompanying drawings. The embodiments and features of the present invention are described and illustrated in conjunction with systems, tools and methods which are meant to exemplify and to illustrate, not being limiting in scope. For purposes of illustration, the exemplary embodiments that follow are discussed in reference to a method in which two fluid flow paths are merged, without substantial mixing, into a flow cell and two detection channels are utilized. It should be understood that the present invention is not limited to methods involving only one or two fluid flow paths and one or two detection channels, and is also applicable to devices and methods involving more than two fluid flow paths and more than two detection channels, and the illustrative embodiments are not meant to be limiting in scope.

Exemplary embodiments illustrate methods for improving accuracy of quantification of particles in a flowing stream through the measurement of flow rates in real or near real time (generically referred to in combination as "real time"), and through both the measurement of flow rates in real time and adjustment of flow rate in real time via a feedback loop. In general, a sample in a liquid medium and a sheath fluid are introduced from two separate flow paths into a single flow cell so as to produce a hydrodynamic focusing of the sample fluid. The flow rate of each fluid may be measured, and also may be controlled via a feedback loop between each fluid flow sensor and a flow control device in each flow path. The flowing sample is then analyzed via an excitation and detection system in a manner so as to enable enumeration of particles such as viruses in the flowing stream.

Figure 1:
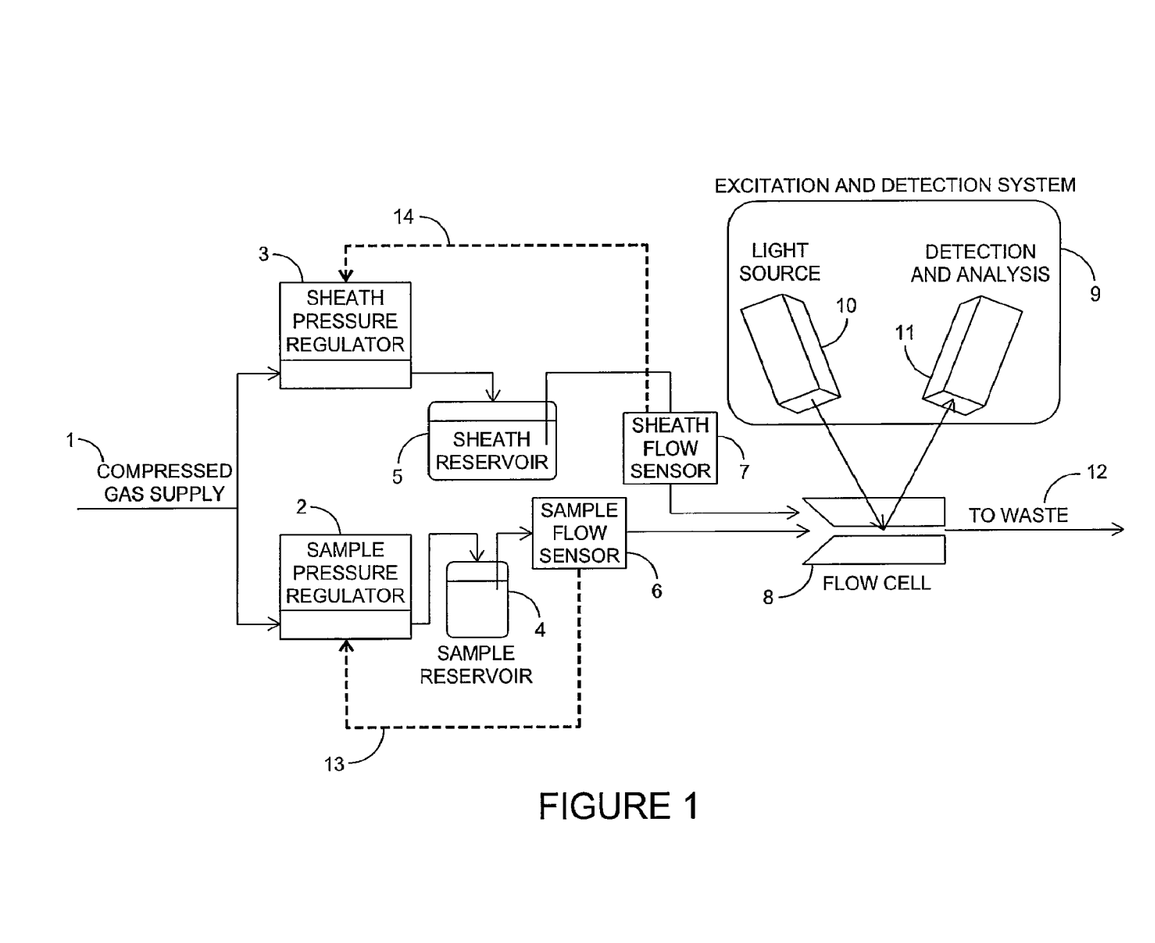
FIG. 1 is a schematic diagram illustrating components of one possible mode of particle enumeration according to embodiments disclosed herein.

FIG. 1 illustrates one possible embodiment of the methods disclosed herein. A compressed gas 1 flows through a sample pressure regulator 2 and sheath pressure regulator 3 configured in parallel, supplying pressure to a sample reservoir 4 and a sheath reservoir 5. While shown as a single compressed gas 1, each flow path may be provided with a gas supply. Sample fluid contained within sample reservoir 4 flows through a sample flow sensor 6, and sheath fluid contained within sheath reservoir 5 flows through a sheath flow sensor 7. A sample fluid flow rate may be measured with sample flow sensor 6, and a sheath fluid flow rate may be measured with sheath flow sensor 7. Sample fluid and sheath fluid merge without mixing and then flow into a flow cell 8 in a manner so as to produce a hydrodynamic focusing effect on the sample fluid. As can be appreciated, hydrodynamic focusing requires the sheath fluid and the sample fluid to have laminar and not turbulent flow. Also, to facilitate hydrodynamic focusing, the sample fluid is generally injected into the middle of the sheath fluid to form a two layer flow through the flow cell 8 where the sheath fluid creates a wall or tube of separate fluid flow around the sample fluid flow. The sample fluid in flow cell 8 is then interrogated by excitation and detection system 9 comprising a light source 10 that impinges the sample fluid, and a detection and analysis system 11. After exiting flow cell 8, both sample fluid and sheath fluid may mix and flow to waste 12.

FIG. 1 also illustrates another possible embodiment of the methods disclosed herein. A compressed gas 1 flows through a sample pressure regulator 2 and sheath pressure regulator 3 configured in parallel, supplying pressure to a sample reservoir 4 and a sheath reservoir 5. Sample fluid contained within sample reservoir 4 flows through a sample flow sensor 6, and sheath fluid contained within sheath reservoir 5 flows through a sheath flow sensor 7. A sample fluid flow rate may be measured with sample flow sensor 6, and a sheath fluid flow rate may be measured with sheath flow sensor 7. A measured sample fluid flow rate can be utilized in feedback loop 13 to change the headspace pressure in sample reservoir 4, thereby changing the sample fluid flow rate in real time. In addition, a measured sheath fluid flow rate can be utilized in feedback loop 14 to change the headspace pressure in sheath reservoir 5, thereby changing the sheath fluid flow rate in real time. If, for example, the sample fluid flow rate is above a predefined threshold flow rate, feedback loop 13 would change the set point on the sample pressure regulator 2 to lower the pressure (and hence flow rate) on sample reservoir 4. If, for example, the sample fluid flow rate is below a predefined threshold flow rate, feedback loop 13 would change the set point on the sample pressure regulator 2 to raise the pressure (and hence flow rate) on sample reservoir 4. Feedback loop 14 would work similarly on the sheath fluid flow path. Alternatively, the feedback loop could operate based on relative flow rates between the sample and sheath fluid path, based on a rate of change of flow rate, or the like. Alternatively, fluid control values may be used to constrict or relax the size of the flow path to control flow rates. Sample fluid and sheath fluid then flow into a flow cell 8 in a manner so as to produce a hydrodynamic focusing effect on the sample fluid. The sample fluid in flow cell 8 is then interrogated by excitation and detection system 9 comprising a light source 10 that impinges the sample fluid and a detection and analysis system 11. After exiting flow cell 8, both sample fluid and sheath fluid combine and flow to waste 12. By maintaining the sample fluid flow rate, at any given moment the volume of sample fluid that has passed through the flow cell is known. Thus, the total number of particles in a given volume is determinable in real time.

Figure 2A:
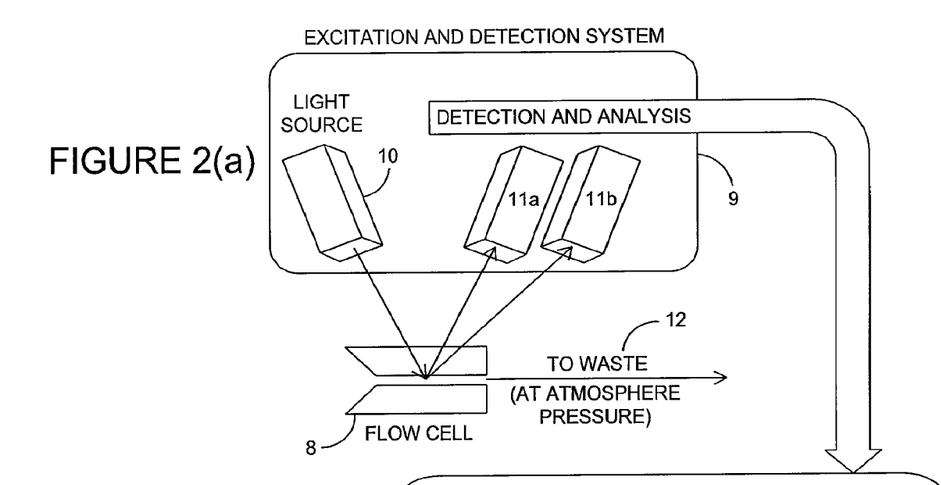
FIG. 2(a) is a schematic diagram illustrating the excitation and detection system for one possible mode of particle enumeration according to embodiments disclosed herein.
Figure 2B:
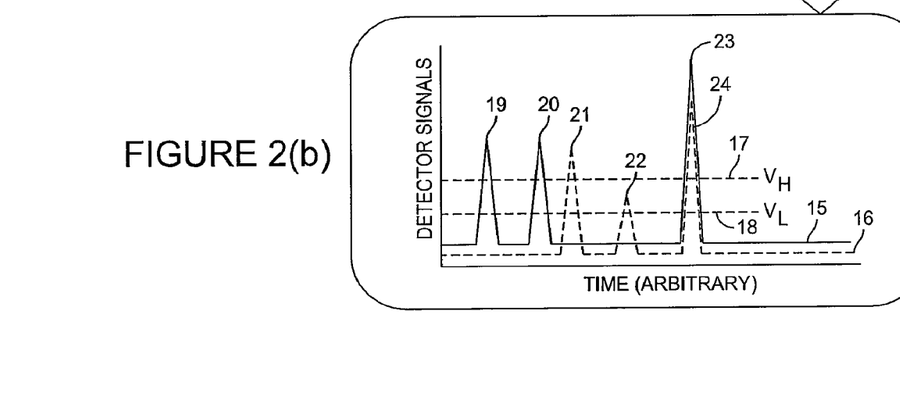
FIG. 2(b) is a graphical representation of a detection model.

To better understand the exemplary embodiments described, it is useful to further describe an excitation and detection system and general counting method that may be utilized in combination with the methods described herein. FIG. 2 schematically illustrates an excitation and detection system 9 comprised of a light source 10 and detection and analysis system 11. Detection and analysis system 11 is described for two detection channels (11a, 11b) as a matter of convenience, however, more or less detection channels are possible. In FIG. 2a, light source 10 impinges on a sample fluid flowing through the center of a flow cell 8. In one embodiment, particles within the sample fluid may be fluorescently labeled to enable enumeration via fluorescence measurement. As a non-limiting example, the nucleic acid and protein of virus particles within a sample fluid may be labeled with two different fluorescent species capable of being differentially detected on two detection channels. An optical system can be used to collect the fluorescence signal being emitted from the particles within the sample fluid. Emitted signal can then be spatially and optically filtered to separate the two different fluorescence signatures to enable detection of these signals on two separate detectors. A schematic illustration of the general output from a system using two detectors as described above is shown in FIG. 2b. Measured signal from one detector is shown as solid line 15, and measured signal from a second detector is shown as dotted line 16. An event on a detection channel may be defined as when the leading edge of the signal is greater than a high reference voltage ($V_H$) 17. The duration of the event is defined by the time the signal is above a low reference voltage ($V_L$) 18. Reference voltages 17 and 18 may be set to ensure that background signals do not constitute an event. As a non-limiting example, solid line 15 represents measured signal from a channel optimized to detect protein passing through a detection volume over an arbitrary time period, and dotted line 16 represents measured signal from a channel optimized to detect nucleic acid passing through a detection volume over the same arbitrary time period. Detection events 19 and 20 represent protein passing through the detection volume, whereas detection event 21 represents nucleic acid passing through the detection volume. Because 22 does not ever exceed $V_H$, 22 is not considered a detection event. Events 23 and 24 occur simultaneously on both detection channels.

The number of detection events on each individual channel as well as the number of simultaneous events may be counted, and these numbers of events can used to calculate to a concentration of particles passing through the detection volume. For the non-limiting example described herein, the number of simultaneous events occurring can be used to calculate the concentration of intact virus particles containing both nucleic acid and protein within a sample fluid. A counting method described above in relation to FIG. 2 can be utilized to measure particle counts in real time, and can be implemented using hardware, software, or a combination of hardware and software.

A number of variables may ultimately affect the sample fluid and sheath fluid flow rates in a method incorporating a hydrodynamic focusing approach. The sample fluid flow rate, which is typically less than ~5000 nL/min for the non-limiting examples described herein, increases when the headspace pressure above the sample fluid in sample reservoir 4 is increased. The sample fluid flow rate may decrease due to greater restriction in the tubing from an intermittent clog, periodic temperature fluctuation, other periodic event, or from a more regular change such as a decrease in tubing diameter. In addition, increasing the sheath fluid flow rate can drastically decrease the sample fluid flow rate due to backpressure variations, so that any variable affecting the sheath fluid flow rate also may affect the sample fluid flow rate. The sheath fluid flow rate increases when the headspace pressure above the sheath fluid in sheath reservoir 5 is increased, and also when the liquid level in sheath reservoir 5 is increased. The sheath fluid flow rate may decrease due to increases in backpressure from restriction of the tubing, atmospheric pressure changes at the waste outlet, or gravimetric forces in that the relative heights of the sample and sheath reservoirs have changed.

Flow Sensor Response Curves

Figure 3:
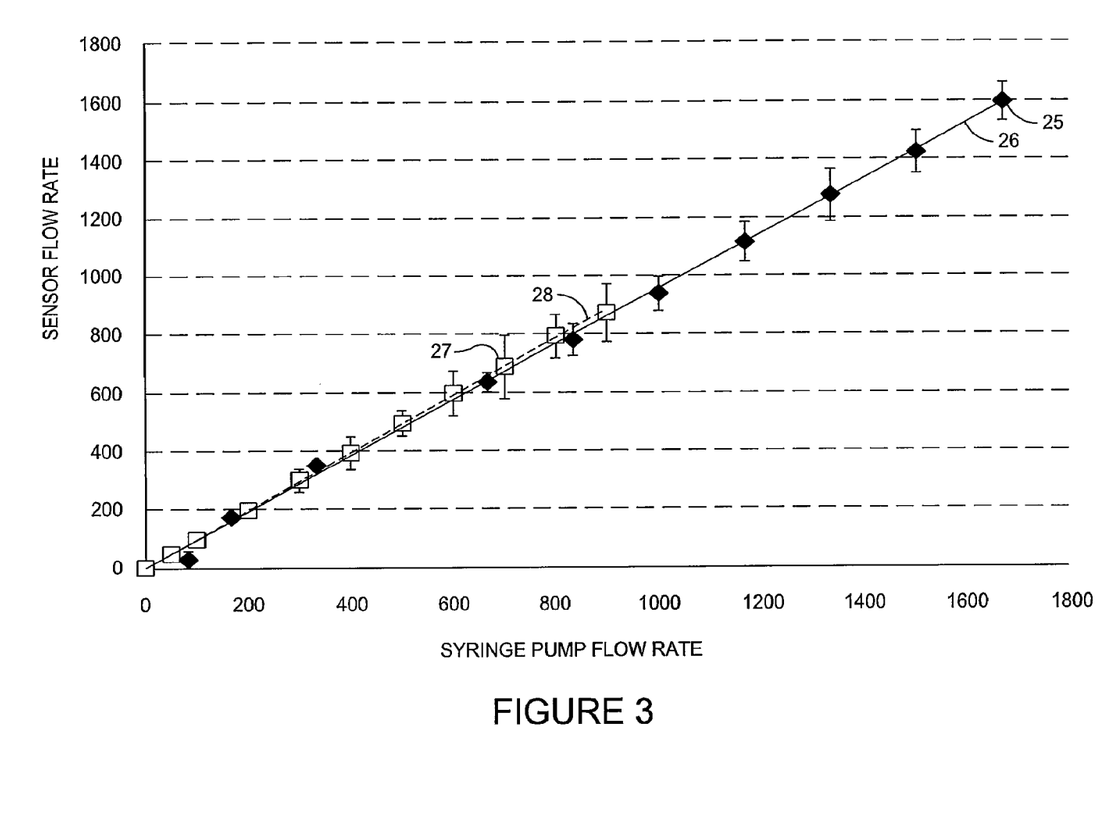
FIG. 3 illustrates a correlation between flow sensor response and a gold standard syringe pump measurement according to embodiments disclosed herein.

FIG. 3 illustrates the accurate operation of both the sample flow sensor 6 and sheath flow sensor 7 by comparing flow rates measured with these sensors to flow rates measured by a standard syringe pump. Sample fluid sensor and sheath fluid sensor used are models LG16-0150A and LG16-1000A, respectively, (Sensirion Inc., Westlake Village, Calif.), and the syringe pump used was model NE-1000 (New Era Pump Systems Inc., Farmingdale, N.Y.). Closed diamonds 25 and solid line 26 show the correlation between sample flow rates measured with sample flow sensor 6 on the y-axis and the syringe pump on the x-axis, both measured in nL/min. The data represented by open squares 27 and dashed line 28 shows the correlation between sheath flow rates measured with sheath flow sensor 7 on the y-axis and the syringe pump on the x-axis, both measured in μL/min. A strong correlation with syringe pump flow rate is observed for both sensors, with $R^2=0.998$ (solid line 26) and $R^2=0.999$ (dashed line 28) for the sample flow sensor and sheath flow sensor data, respectively.

Flow Rate Variation with Constant Applied Pressure

Figure 4:
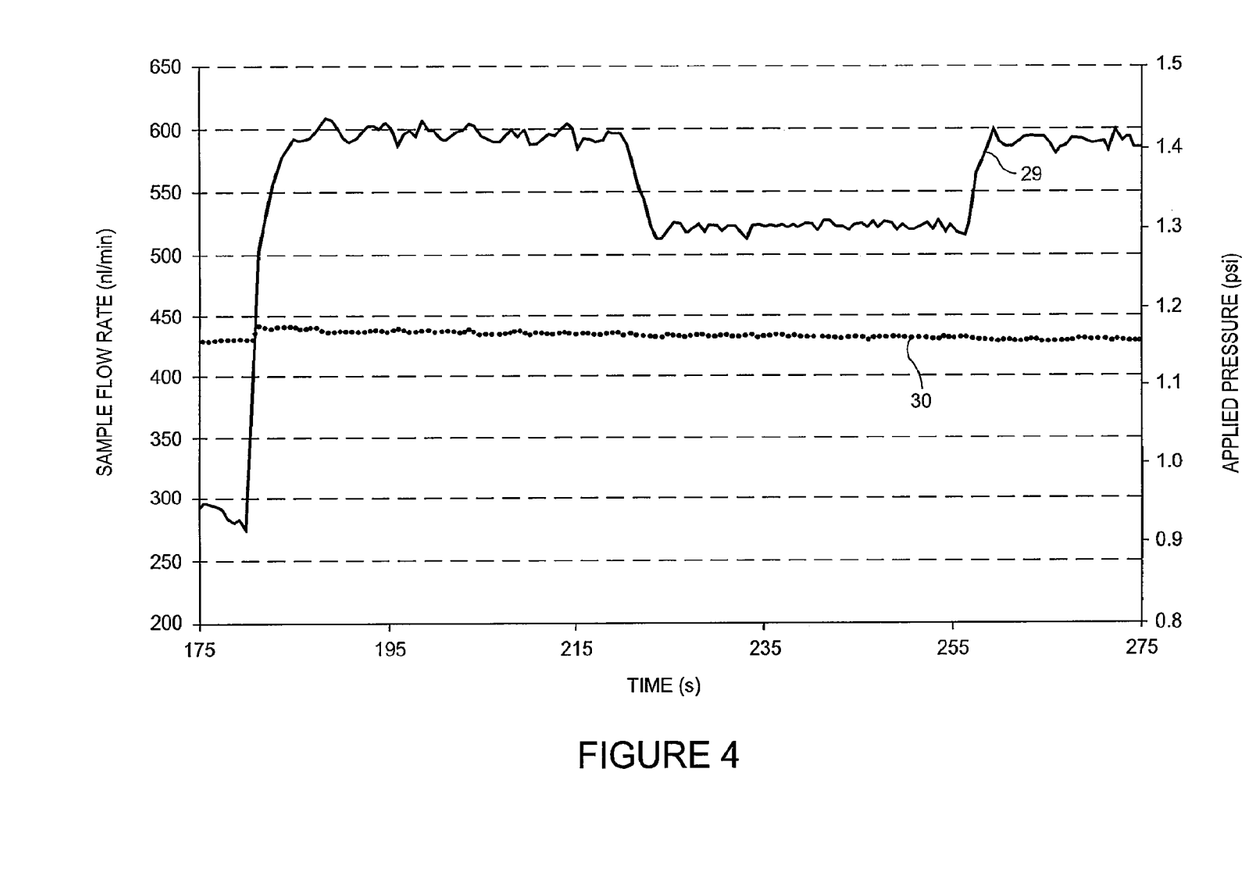
FIG. 4 illustrates sample fluid flow rate fluctuations are possible during the application of a constant sample fluid headspace pressure according to embodiments disclosed herein.

FIG. 4 illustrates the problem with the commonly made assumption that a constant applied pressure delivers a constant flow rate. Sample flow rate in nL/min shown on the left-hand y-axis corresponds to the data series represented by solid line 29, whereas applied pressure in psi on the right-hand y-axis corresponds to the data series represented by dotted line 30. As a function of time in seconds along the x-axis, FIG. 4 shows that although a constant pressure is being applied to the headspace in sample reservoir 4 using sample pressure regulator 2, the measured flow rate of the sample fluid is highly variable shown by solid line 29. This change in flow rate can be caused by clogs within the system other periodic or unexpected events as described above. The particle concentration in solution can be calculated by determining the number of qualifying detection events that pass through the detection volume in a certain time period. Therefore, if the sample flow rate is assumed rather than measured and/or controlled over that same time period, the ultimate calculated particle concentration is affected by changes in flow rate such as those observed in FIG. 4.

Figure 5:
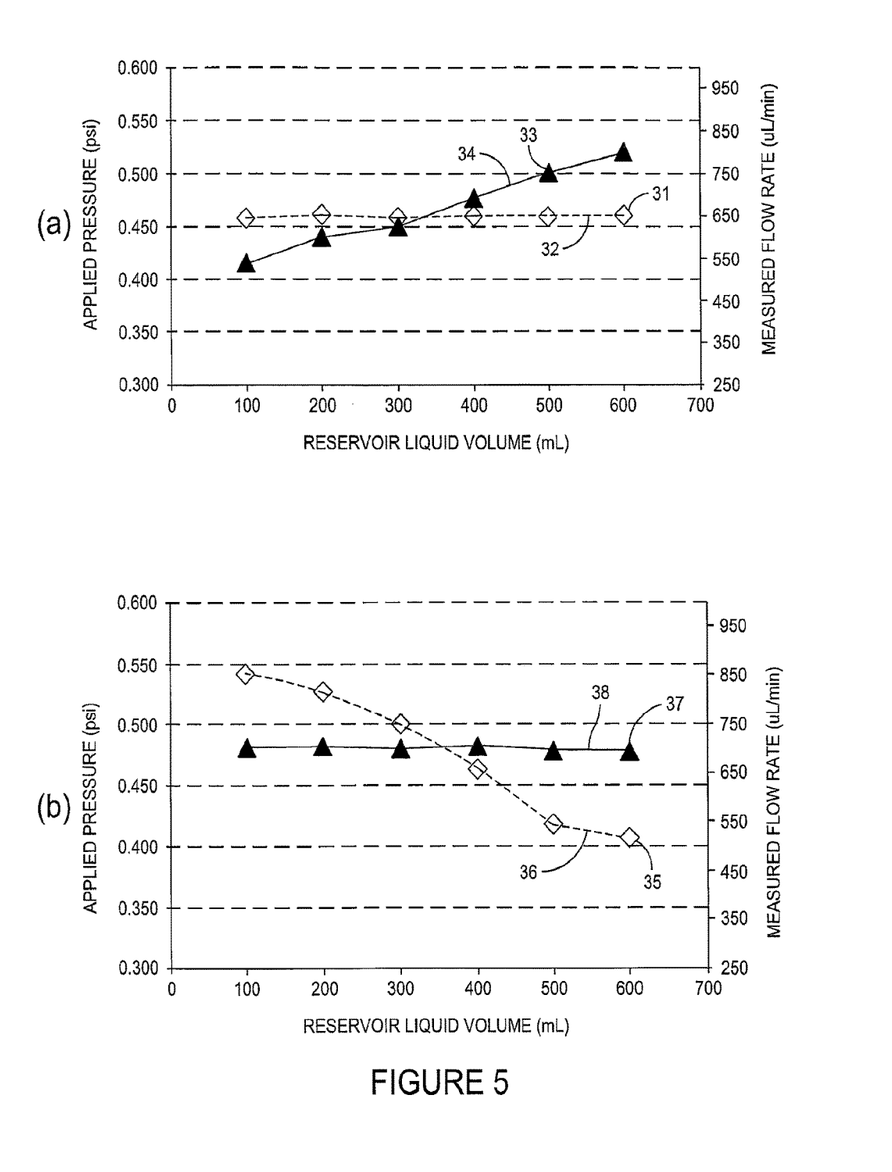
FIG. 5(a) illustrates the sheath fluid flow rate fluctuations possible during the application of a constant sheath fluid headspace pressure according to embodiments disclosed herein.
FIG. 5(b) illustrates a constant flow rate delivered if a feedback loop is used to control the applied pressure.

FIG. 5a illustrates that applying a constant pressure with sheath pressure regulator 3 to the headspace in sheath reservoir 5 is not sufficient to deliver a constant sheath flow rate. Although the pressure applied to the headspace in sheath reservoir 5 remains constant as shown by open diamonds 31 and dashed line 32 (left-hand y-axis, measured in psi), as the volume measured in mL in the sheath reservoir is increased there is a steady increase in the flow rate measured by sheath flow sensor 7 shown by closed triangles 33 and solid line 34 (right-hand y-axis in μL/min).

FIG. 5b illustrates that flow rate measurement utilized in conjunction with a feedback loop to compensate for changes in the measured flow rate can be utilized to delivery a constant flow rate. Sheath flow sensor 7 was utilized to measure the sheath flow rate, and feedback loop 14 was utilized to apply changes to the headspace pressure to compensate for the measured changes in sheath flow rate. With feedback control, open diamonds 35 and dashed line 36 indicate that the applied pressure over the headspace (left-hand y-axis, measured in psi) was automatically decreased to compensate for the pressure differences that resulted from increased volume in sheath reservoir 5. The improvement in the flow rate delivered due to the ability of the feedback loop to provide compensation is shown by the constant measured sheath flow rate (right-hand y-axis, measured in μL/min) shown by closed triangles 37 and solid line 38.

Sheath Fluid Flow Rate Effect on Sample Fluid Flow Rate

Figure 6:
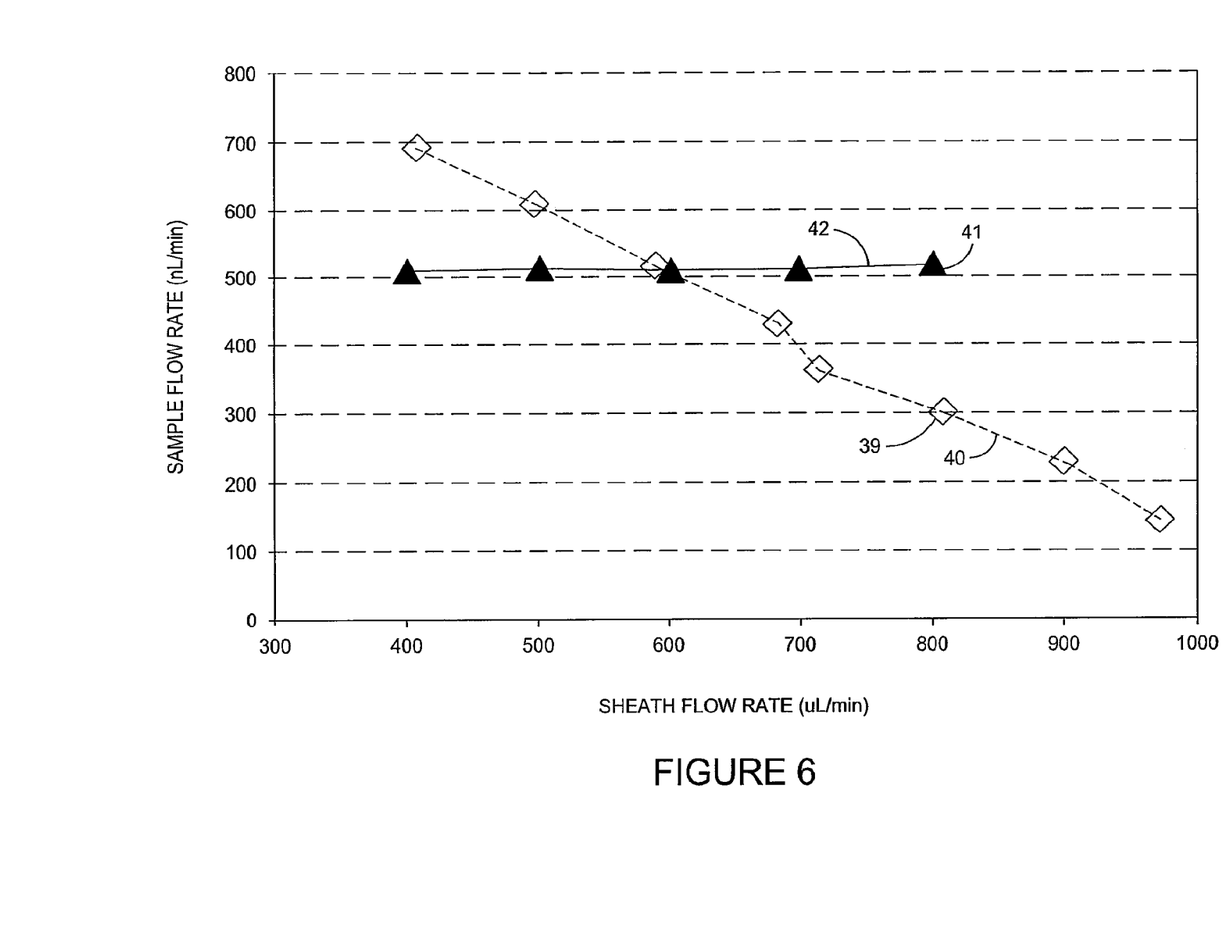
FIG. 6 illustrates an anticorrelation between sheath fluid flow rate and sample fluid flow rate according to one possible mode of particle enumeration according to embodiments disclosed herein.

FIG. 6 illustrates the strong correlation between sheath fluid flow rate in pμL/min on the x-axis and sample fluid flow rate in nL/min on the y-axis. Although a constant pressure may be applied to the headspace over the sample fluid in sample reservoir 4 using sample pressure regulator 2, if the sheath fluid flow rate is changed, the sample fluid flow rate also changes as illustrated by open diamonds 39 and dotted line 40 showing that sheath fluid flow rate and sample fluid flow rate are anticorrelated due to increased backpressure in the sample stream at higher sheath fluid flow rates. However, the measured sample fluid flow rate may be utilized in feedback loop 13 to change the headspace pressure in sample reservoir 4 in order to supply a sample fluid flow rate that will remain constant, regardless of the sheath fluid flow rate. This feedback-controlled situation is illustrated with measurements of sample flow rate represented by closed triangles 41 and solid line 42 which indicate a constant sample flow rate as the sheath fluid flow rate is varied.

Measuring Flow and Correcting for Flow Fluctuations Improves Quantification

Figure 7:
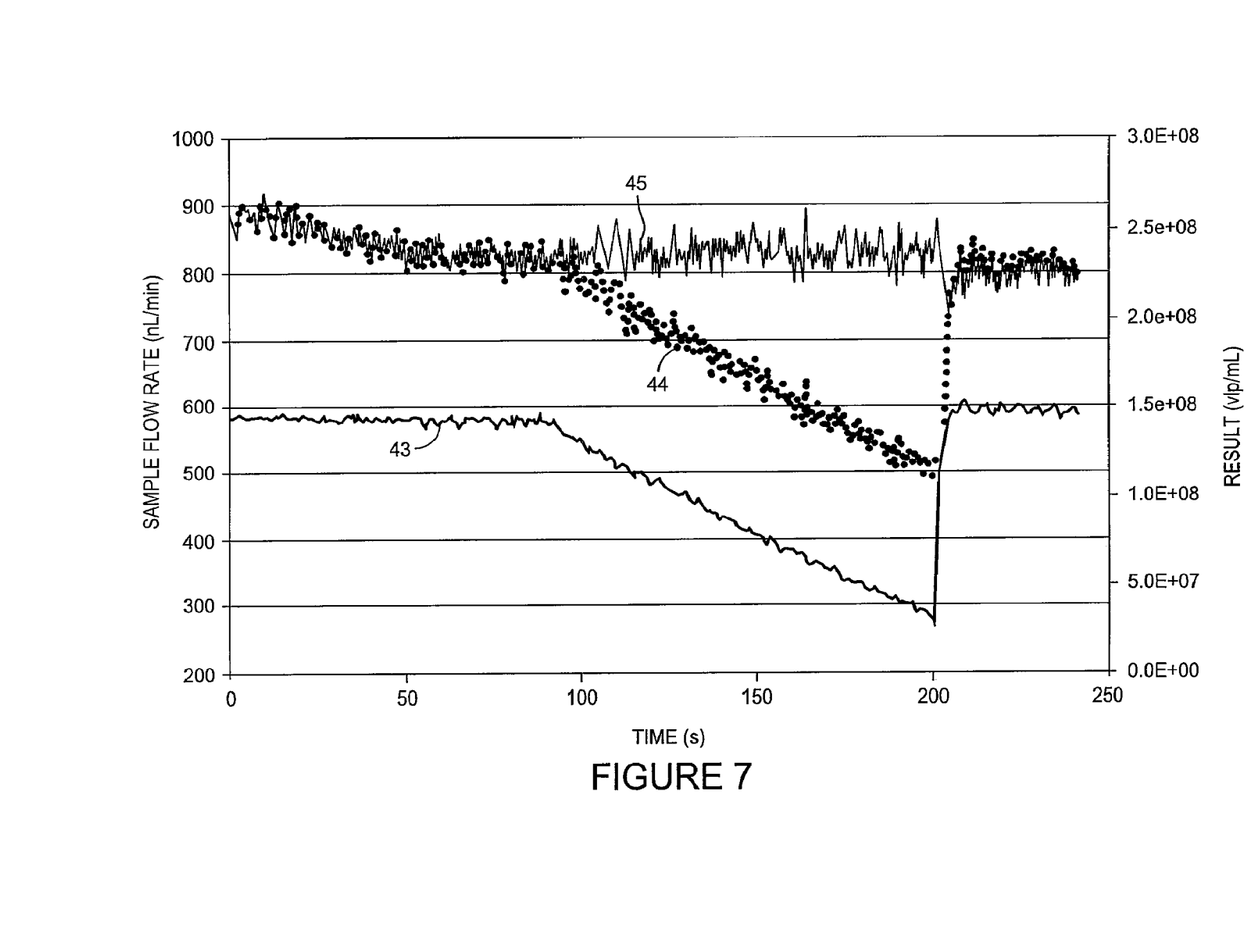
FIG. 7 illustrates the differences in calculated particle concentration using an assumed sample fluid flow rate based on a constant applied pressure, and using the sample fluid flow rate measured during the time course of the experiment.

FIG. 7 shows the difference in calculated concentrations that are obtained depending on whether or not the measured sample fluid flow rate is used to correct for flow fluctuations that occurred during the time course in seconds (x-axis) of an experimental run. As is common in flow cytometry, the sample pressure was set to a constant value of 1.163±0.006 psi. Solid line 43 shows that some event during the timeframe of the experiment caused an approximate 50% drop in sample flow rate (left-hand y-axis, measured in nL/min). If the applied sample pressure is used to assume a constant sample fluid flow rate, and this constant sample fluid flow rate is in turn used to calculate the sample concentration (shown on the right-hand y-axis, measured in vpl/mL where vpl is virus-like particles), the calculated sample concentration over the time of the experiment shown by dotted line 44 is obtained and mimics the time profile of the sample fluid flow rate. However, solid grey line 45 illustrates the concentration measurement that is obtained if the sample fluid flow rate measured over the timeframe of the experiment is used to correct for this fluctuation in flow. The average particle concentration calculated for dotted line 44 is $2.1 \times 10^8$ vlp/ml, with a relative standard deviation of ~19% ($\pm 0.4 \times 10^8$ vlp/ml). The average particle concentration calculated for solid grey line 45 is $2.4 \times 10^8$ vlp/mL with a relative standard deviation of only ~4% ($\pm 0.1 \times 10^8$). When sample fluid flow rate is controlled, the calculated sample concentration is more stable and relatively constant over the timeframe of the experiment with a significantly lower relative standard deviation. If the sample fluid flow rate is not controlled to be a constant, the vpl/ml result will generally be artificially high or low depending on whether the flow rate is high or low. This corrected concentration result is clearly an improvement over the situation where the sample fluid flow rate is not measured and/or corrected for. The use of a measured sample fluid flow rate to correct for flow fluctuations in calculating sample concentration was done in this case as a post-acquisition processing step. As shown by the next figure, this compensation for flow fluctuation also can be done in real time through the use of feedback loops to similarly improve particle quantification accuracy.

Measuring and Controlling Flow in Real-Time Similarly Improves Quantification

Figure 8A:
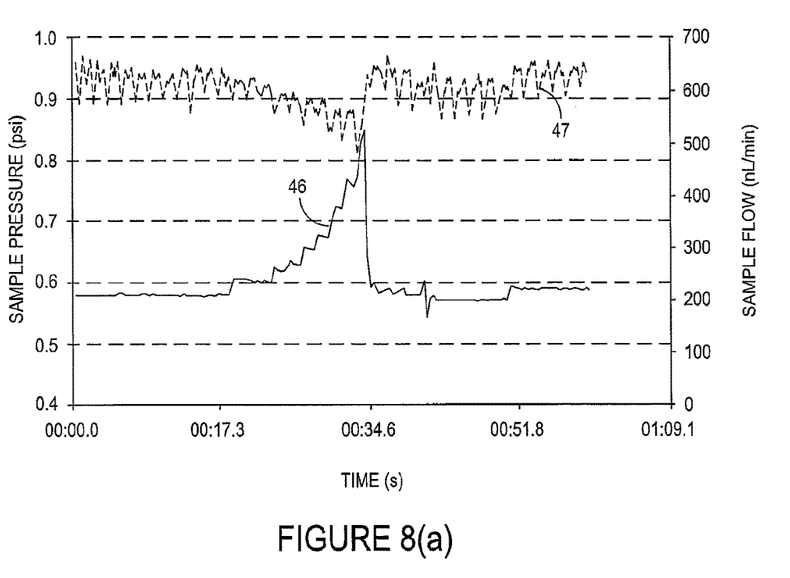
FIG. 8(a) illustrates the constant sample fluid flow rate delivered if a feedback loop is utilized to control the applied sample pressure during the run.
Figure 8B:
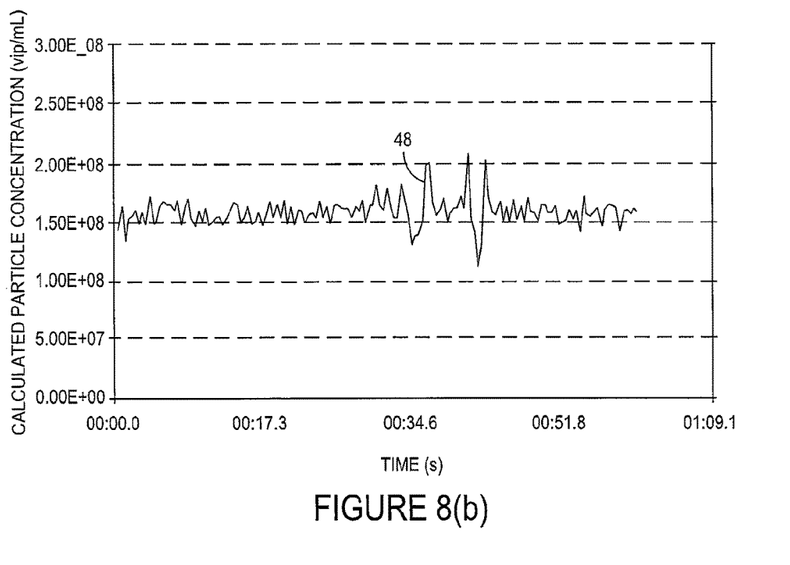
FIG. 8(b) illustrates the calculated particle concentration.

FIG. 8 illustrates that flow rate measurement combined with correcting for fluctuations in real-time via a feedback loop can provide an 'instantaneous' improvement in particle quantification accuracy. In the experiment illustrated in FIG. 8a, feedback loop 14 was used to control the sheath fluid flow rate by controlling the headspace pressure in sheath reservoir 5 via sheath pressure regulator 3. In addition, feedback loop 13 was used to control the sample fluid flow rate by controlling the headspace pressure in sample fluid reservoir 4 via sample pressure regulator 2. An event disrupted the sample fluid flow rate, and required feedback loop 13 to supply a variable pressure over the headspace in sample fluid reservoir 4, illustrated by solid line 46 (measured in psi, right-hand y axis). This variable applied pressure resulted in the delivery of the relatively constant sample fluid flow rate in nL/min illustrated by dotted line 47 (right-hand y-axis).

FIG. 8b illustrates the result when the measured sample fluid flow rate 47 in FIG. 8a was utilized in real time to calculate the particle concentration in the sample (illustrated by solid line 48, y-axis in vpl/mL). Because the amount of fluid flowing past the excitation and detection system 9 was known, post process analysis was not necessary to qualify the results such that real time vpl may be obtained. The average particle concentration over the time course of this experiment is $1.6 \times 10^8$ vlp/mL with a relative standard deviation of ~6% ($\pm 0.1 \times 10^8$ vlp/mL). This relative standard deviation is similar to that shown in FIG. 7 for the case where the concentration is calculated from the corrected sample flow rate. Both measuring and controlling the sample fluid flow rate in real-time through the use of a feedback loop results in particle quantification with improved accuracy compared to a situation in which an uncorrected flow rate is used to calculate particle concentration. In addition, correcting for sample fluid flow rate fluctuations during the run allows a concentration result to be displayed in real time, eliminating the majority of post data collection processing and decreasing overall time to result. Thirdly, using a second feedback loop to provide a constant sheath fluid flow rate has the additional advantage of stabilizing the hydrodynamic focusing effect, and further improving particle quantification.

We claim:

1. A method for analyzing sample fluid for presence of free virus in solution, the method comprising:
    flowing a sample fluid comprising liquid and a plurality of particles of a size smaller than 1 micron, wherein the particles are individual fluorescently-labeled virus particles from a sample reservoir under pressure from a compressed gas applied to the sample reservoir to and through a flow cell, comprising controlling the sample fluid flow rate to the flow cell at less than 5000 nanoliters per minute;
    measuring the sample fluid flow rate to the flow cell with a sample flow sensor coupled with a sample pressure regulator through a sample feedback control loop;
    the controlling the fluid sample flow rate comprising feedback control through the sample feedback control loop of the sample pressure regulator to control pressure of the compressed gas applied to the sample reservoir based on measured sample fluid flow rate from the sample flow sensor during the measuring;
    merging the sample fluid flow with a sheath fluid flow prior to the flow cell;
    providing the sheath fluid flow from a sheath reservoir under pressure from compressed gas applied to the sheath reservoir;
    prior to the merging, measuring the sheath fluid flow rate with a sheath flow sensor coupled with a sheath pressure regulator through a sheath feedback control loop;
    controlling the sheath fluid flow rate to the merging, the controlling the sheath fluid flow rate comprising feedback control through the sheath feedback control loop of the sheath pressure regulator to control the pressure of the compressed gas applied to the sheath reservoir based on measured sheath fluid flow rate from the measuring the sheath fluid flow rate;

interrogating the sample fluid flow through the flow cell, the interrogating comprising:
- excitation of the sample fluid flow in the flow cell by a light source of an excitation and detection system coupled with the flow cell; and
- detection by a detection and analysis system of the excitation and detection system of only fluorescent response of the sample fluid flow in the flow cell to the excitation;

counting by the detection and analysis system a number of fluorescent response detection events occurring during the detection that are indicative of the presence of a said individual fluorescently-labeled virus particle in the sample fluid flow;

calculating by the detection and analysis system a concentration for virus particles in a volume of the sample fluid interrogated in the flow cell using the counted number of detection events and measured sample fluid flow rate data from the measuring that correspond with the volume of the sample fluid, wherein the detection and analysis system performs the counting and the calculating in real time or near real time of the interrogating; and displaying concentration results of the calculating in the real time or near real time;

wherein the individual fluorescently-labeled virus particles within the fluid sample are fluorescently labeled with different fluorescent species for virus nucleic acid and virus protein, and the detection comprises detecting on separate detection channels for fluorescent responses of the different fluorescent species; and wherein the calculating a concentration for virus particles comprises correcting for sample fluid flow rate fluctuations using the measured sample fluid flow rate data.

* * * * *

UNITED STATES PATENT AND TRADEMARK OFFICE
CERTIFICATE OF CORRECTION

PATENT NO. : 10,031,061 B2
APPLICATION NO. : 13/319662
DATED : July 24, 2018
INVENTOR(S) : Kathy L. Rowlen et al.

Page 1 of 1

It is certified that error appears in the above-identified patent and that said Letters Patent is hereby corrected as shown below:

Column 8, Line 66, the text "pµL/min" should read --µL/min--.

Signed and Sealed this
Fourth Day of September, 2018

Andrei Iancu
*Director of the United States Patent and Trademark Office*